(12) United States Patent
Morita et al.

(10) Patent No.: US 6,329,337 B1
(45) Date of Patent: Dec. 11, 2001

(54) ADHESIVE FOR BIOLOGICAL TISSUE

(75) Inventors: Yasunobu Morita; Ken Murayama, both of Osaka (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/545,171

(22) Filed: Apr. 6, 2000

(30) Foreign Application Priority Data

Apr. 7, 1999 (JP) .................................................. 11-100153

(51) Int. Cl.⁷ ............................ A61K 38/28; C07K 14/00
(52) U.S. Cl. ................................ 514/4; 530/362; 530/363
(58) Field of Search .................. 514/21, 2, 4; 424/78.82; 530/362, 363; 525/54.1, 54.2, 54.21

(56) References Cited

U.S. PATENT DOCUMENTS 4,363,801 * 12/1982 Nagyvary .............................. 424/180

5,583,114 12/1996 Barrows et al. ....................... 514/21

FOREIGN PATENT DOCUMENTS

| 0 570 916 | 11/1993 | (EP) . |
| 94/01508 | 1/1994 | (WO) . |

OTHER PUBLICATIONS

Otani et al., "A New Biological Glue from Gelatin and Poly(L–Glutamic Acid)," *Journal of Biomedical Materials Research*, 13, 157–166 (1996).

* cited by examiner

Primary Examiner—Karen Cochrane Carlson
(74) Attorney, Agent, or Firm—Leydig, Voit & Mayer, Ltd.

(57) ABSTRACT

An adhesive for biological tissue includeds: a glue agent and a cross-linking agent. The glue agent contains a recombinant human plasma protein as a main component. The cross-linking agent contains a bifunctional or multifunctional aldehyde as a main component.

8 Claims, No Drawings

ADHESIVE FOR BIOLOGICAL TISSUE

BACKGROUND OF THE INVENTION
1. Field of the Invention

The present invention relates to an adhesive for biological tissue. More particularly, the present invention relates to an adhesive for biological tissue containing a glue agent and a cross-linking agent, such that the glue agent contains a recombinant human plasma protein as a main component, and that the cross-linking agent contains a bifunctional or multifunctional aldehyde an a main component, the adhesive providing excellent hemostatic and adhesion properties and being biologically absorbable and highly safe.
2. Description of the Related Art Conventionally, various adhesives have been proposed as adhesives for biological tissue. Among others, cyanoacrylate type adhesives (e.g., Aronalpha A from ToaGosei Industry Co., Ltd. and Biobond from Yoshitomi Pharmaceutical Industries, Ltd.), fibrin glues (e.g., Tisseel from Nippon Zoki K.K., Beriplast from Hoechst, and Bolheal from The Chemo-Sero-Therapeutic Research Institute), and gelatin-resorcin-(bifunctional or multifunctional) aldehyde type adhesives (e.g., Cardial GRP Glue from Cardial (France)) are used in actual clinical applications. (See for example, Journal of Biomedical Materials Research, vol. 31, 157–166 (1996).)

The features of conventional tissue adhesives which are used for clinical purposes will now be summarized. First, cyanoacrylate type adhesives provide good adhesion speed and adhesion strength. However, this type of adhesives have significant problems in that flexibility is lost from the adhesion surface obtained by using this type of adhesives, and substances which may pose safety hazards might be produced through in vivo-degradation. Fibrin glues are considered free from safety concerns associated with in vivo-degradation products since they are of biological origin. However, fibrin glues have problems in that they provide somewhat lower adhesion strength. Also, the possibilities of viral infection associated with the use of fibrin glues are non-negligible. Gelatin-resorcin-aldehyde type adhesives provide good adhesion strength. However, this type of adhesive also has problems in that some products employ highly-toxic formaldehyde as an aldehyde, and that gelatin is not entirely free from prion infection possibilities.

Adhesives containing a plasma protein obtained from blood, e.g., serum albumin, and a bifunctional or multifunctional aldehyde have been proposed and are known to provide good adhesion strength (See, for example, PCT Publication WO04/01508; this publication is incorporated herein by reference). Some of these adhesives are used for clinical purposes in Europe. However, this type of adhesives are not entirely free from safety concerns because there are possibilities of infection with viruses from human or animal blood products or derivatives. Therefore, those who are engaged in clinical practice are awaiting the development of an adhesive for biological tissue which provides good adhesion strength and yet is highly safe.

SUMMARY OF THE INVENTION

An adhesive for biological tissue according to the present invention includes: a glue agent and a cross-linking agent, wherein the glue agent contains a recombinant human plasma protein as a main component, and wherein the cross-linking agent contains a bifunctional or multifunctional aldehyde an a main component.

In one embodiment of the invention, the recombinant human plasma protein is human serum albumin.

In another embodiment of the invention, the glue agent is substantially free of components derived from a host cell from which the recombinant human serum albumin was produced or any other contaminants, and the coloration of the glue agent is at a minimum level.

In still another embodiment of the invention, the bifunctional or multifunctional aldehyde is selected from a group including glyoxal, succinaldehyde, glutaraldehyde, and malealdehyde.

In still another embodiment of the invention, the glue agent contains a further component for enhancing the cross-linking rate and/or for adjusting the viscosity of the glue agent.

In still another embodiment of the invention, the further component includes a chitosan which is used for medical purposes.

An adhesive kit for biological tissue according to the present invention includes: a first container containing recombinant human serum albumin as a main component; and a second container containing an aldehyde as a main component.

Thus, the present invention provides an adhesive for biological tissue containing a glue agent and a cross-linking agent, wherein the glue agent contains a recombinant human plasma protein as a main component, and wherein the cross-linking agent contains a bifunctional or multifunctional aldehyde as a main component.

The recombinant human plasma protein may preferably be human serum albumin, and may more preferably be high-purity human serum albumin. Human serum globulin may also used. The human serum albumin may be high-purity human serum albumin which is purified by a method described in, for example, U.S. Pat. No. 5,440,018 and 5,521,287 (the entire disclosure thereof is incorporated herein by reference for this disclosure), which is substantially free of components derived from a host call from which the recombinant human serum albumin was produced or any other contaminants, and whose coloration is sufficiently controlled. In such cases, the purity of the high-purity human serum albumin is preferably 99.999999%, and more preferably 99.9999999%. The degree of coloration may be in the range of 0.01 to 0.05 for $A_{350}/A_{280}$ ratio, for example.

The bifunctional or multifunctional aldehyde may be a dialdehyde selected from a group including glyoxal, succinaldehyde, glutaraldehyde, and malealdehyde.

The present invention also provides an adhesive kit for biological tissue including a first container containing a glue agent which contains a recombinant human plasma protein as a main component, and a second container containing a cross-linking agent which contains a bifunctional or multifunctional aldehyde as a main component, and optionally an explanation manual for the kit.

In accordance with the adhesive for biological tissue according to the present invention, a plasma protein which is obtained through gene recombinant techniques, preferably human serum albumin, and more preferably high-purity human serum albumin, is used as a main component of a glue agent. As a result, not only can infection with viruses of from human or animal blood products or derivatives be prevented, but it is also possible to provide an adhesive for biological tissue having stable quality. The adhesive for biological tissue according to the present invention also permits stable mass production without depending on supplies of animal or human blood. As the bifunctional or multifunctional aldehyde, it is preferable to use glutaraldehyde and/or glyoxal, which have conventionally been used in cardiovascular surgery and the like, instead of highly-toxic formaldehyde.

The recombinant human serum albumin which is used as a main component of the glue agent of the present invention may be produced by a known method using a known human serum albumin sequence. It will be readily understood by those skilled in the art that a serum albumin sequence having at least one of substitution, deletion, and/or addition of one or more (preferably not all) amino acids may also be used to produce the human serum albumin which is used as the glue agent of the adhesive according to the present Invention.

For example, a host for producing human serum albumin may be prepared by a known method, and the host is cultured by a known culture method (See, for example, U.S. Pat. No. 5,440,018 and 5,521,287, the entire disclosure of which is incorporated herein by reference for this disclosure). Examples of host cells include, without limitation, bacterial cells (e.g., *E. coli*), yeast cells (e.g., *Pichia pastoris*, and *Saccharomyces cerevisiae*), and mammalian cells. After the recombinant human serum albumin of interest is obtained, the human serum albumin is subjected to adequate purification processes (e.g., that mentioned above) so as to remove any components related to the host cells or other contaminants and to minimize coloration. The recombinant high-purity human serum albumin for use in the present invention is characterized as a single substance having a molecular weight of about 67,000 which is substantially free of dimers, polymers, or any decomposed matters that have a molecular weight of about 43,000. Furthermore, the recombinant high-purity human serum albumin is substantially free of any contaminants (e.g., polysaccharides) derived from the host cells, especially those having an antigenic nature. For example, the amount of fatty acids which are bound to the human serum albumin is equal to or less than 1 molecule per human serum albumin molecule, and preferably equal to or less than 0.1 molecules per human serum albumin molecule (See, for example, U.S. Pat. No. 5,440,018 and 5,521,287, the entire disclosure of which is incorporated herein by reference for this disclosure).

As the cross-linking agent for use in the present invention, a bifunctional or multifunctional aldehyde may be used, especially a dialdehyde selected from a group including glyoxal, succinaldehyde, glutaraldehyde, and malealdehyde. Other suitable cross-linking agents which have low toxicity include multifunctional aldehydes derived from naturally-occurring substances, e.g., dextrandialdehyde, saccharides which are oxidized by m-periodate, Genipin, and the like.

It is also possible to add optional components, other than recombinant human serum albumin, to the adhesive according to the present invention in order to enhance the cross-linking rate through reactions with aldehydes. Alternatively or additionally, it is also possible to add optional components, other than recombinant human serum albumin, to the adhesive according to the present invention in order to adjust the viscosity of the glue agent. Examples of such optional components include chitosans which are used for medical purposes due to their excellent safeness: e.g., partially-acetylated chitosan, preferably a 50% acetylated chitosan, and partially-deacetylated carboxymethylchitin.

The glue agent for use in the present invention contains a recombinant human plasma protein as a main component. The concentration of the recombinant human serum albumin is preferably in the range of about 20 wt % to about 55 wt %, more preferably in the range of about 30 wt % to about 50 wt %, and most preferably in the range of about 40 wt % to about 45 wt %. In the case where chitosans are added to the recombinant human serum albumin, the concentration of the chitosans is preferably in the range of about 0.1 wt % to about 10 wt %, more preferably in the range of about 0.5 wt % to about 5 wt %, and most preferably in the range of about 0.5 wt % to about 2 wt %.

The concentration of the bifunctional or multifunctional aldehyde for use in the present invention is preferably in the range of about 1 wt % to about 20 wt %, more preferably in the range of about 2.5 wt % to about 15 wt %, and most preferably in the range of about 5 wt % to about 10 wt %.

The adhesive according to the present invention can be prepared as follows. The glue agent which contains a recombinant human serum albumin as a main component can be prepared in the form of an aqueous solution which is filled in a container under aseptic conditions. Alternatively, an aqueous solution of the glue agent may be filled in a container (e.g., a vial) under aseptic conditions and then sterilized. Alternatively, the above aqueous solution of the glue agent may be lyophilized, and, prior to use, the lyophilized glue agent may be reconstituted with water or saline for injection, or the like. The cross-linking agent may be prepared by filling an aqueous solution of one or more kinds of bifunctional or multifunctional aldehyde in a container under aseptic conditions. Alternatively, an aqueous solution of an appropriate aldehyde may be first filled in a container and then subjected to sterilization.

When the adhesive for biological tissue according to the present invention is used in an actual procedure for adhering pieces of biological tissue, the glue agent is first applied to the biological tissue of interest, and then the cross-linking agent is added thereto, followed by pressurization of the adhesion site to effect curing, as in the manner of using any known adhesive. The concentration of the cross-linking agent, and the amount of cross-linking agent added relative to the glue agent may vary depending on the composition and/or concentration of the specific glue agent used, but is preferably set at a value which enables sufficient curing within a period of about 1 to about 5 minutes. Such adjustment is within the skill of those skilled in the art.

According to the present invention, the glue agent and the cross-linking agent may be separately filled in a vial or a syringe, and sealed with packaging materials which do not allow transmission of oxygen, with a deoxydation agent and the like also sealed as necessary.

DESCRIPTION OF THE PREFERRED EMBODIMENTS

Hereinafter, the present invention will be described in more detail by way of examples.

EXAMPLE 1

A 45 wt % aqueous solution of recombinant human serum albumin was prepared. A 10 ml syringe made of polypropylene/polyethylene was filled with the aqueous solution of recombinant human serum albumin, sealed within a sterilization bag, and thereafter subjected to an ethyleneoxide sterilization process following a standard procedure (hereinafter this resultant solution will be referred to as "glue agent A"). Next, 5 ml syringes made of polypropylene/polyethylene were filled with aqueous solutions containing glutaraldehyde in the amount of 10 wt %, 5 wt %, or 2.5 wt %, similarly sealed, and thereafter subjected to ethyleneoxide sterilization in a similar manner.

EXAMPLE 2

An aqueous solution containing recombinant human serum albumin in the amount of 25 wt % and 50%- acetylated chitosan (KOYO CHITOSAN DAC-50 from Koyo Chemical K.K.) in the amount of 0.5 wt % was prepared, placed in a syringe, and thereafter subjected to sterilization as described in Example 1 (hereinafter this resultant solution will be referred to as "glue agent B").

EXAMPLE 3

An aqueous solution containing recombinant human serum albumin in the amount of 30 wt % and partially-deacetylated carboxymethylchitin (KOYO CM CHITIN from Koyo Chemical K.K.) in the amount of 5 wt % was prepared, placed in a syringe, and thereafter subjected to sterilization an described in Example 1 (hereinafter this resultant solution will be referred to as "glue agent C").

Adhesion Strength Test

A commercially available bovine pericardial patch (Tissue Card from Senko Medical Instrument mfg. Co., Ltd.) was out into pieces each measuring 1 cm×5 cm, which were used as adhesion strength test samples. The moisture on the surface of each test sample was minimized by absorbing with filter paper. In an area measuring 1 cm$^2$ on each test sample, 0.1 g of one of the glue agents prepared according to Examples 1 to 3 was applied, and 10 μl of a cross-linking agent prepared according to Example 1 was added at a predetermined concentration. Immediately thereafter, another test sample was attached to each test sample in an adhesion area measuring 1 cm$^2$. A weight (100 g) was placed over the adhesion area to apply pressure. After the lapse of two minutes, the weights were removed, and the samples were left quiet for five more minutes. Then, the samples were subjected to tensile tests by using a tensile test apparatus (TENSILON RTM100 manufactured by TOYO BALDWIN; tensile speed: 3 cm/min). For comparison, similar tests were also conducted using a conventional fibrin glue (Bolheal from Chemo-Sero-Therapeutic Research Institute). The results of these tests are shown in Table 1 below.

TABLE 1

| | Tensile test results | | |
|---|---|---|---|
| Test No. | Glue agent | Concentration of Cross-linking agent | Tensile strength (g/cm$^2$) |
| 1 | A | 2.5 wt % | 600 |
| 2 | A | 5.0 wt % | 750 |
| 3 | A | 10.0 wt % | 1,200 |
| 4 | B | 2.5 wt % | 800 |
| 5 | B | 5.0 wt % | 1,000 |
| 6 | C | 2.5 wt % | 650 |
| 7 | C | 5.0 wt % | 800 |
| 8 | conventional fibrin glue (Bolheal) | | 200 |

Various other modifications will be apparent to and can be readily made by those skilled in the art without departing from the scope and spirit of this invention. Accordingly, it is not intended that the scope of the claims appended hereto be limited to the description an set forth herein, but rather that the claims be broadly construed.

What is claimed is:

1. An adhesive for biological tissue comprising: a glue agent and a cross-linking agent, wherein the glue agent contains a recombinant human serum albumin, which is free of dimers, polymers, and any decomposed matters that have a molecular weight of about 43,000 and is free of infectious agents, as a main component, and wherein the cross-linking agent contains a bifunctional or multifunctional aldehyde as a main component.

2. An adhesive for biological tissue according to claim 1, wherein the glue agent is free of components derived from a host cell from which the recombinant human serum albumin was produced or any other contaminants, and wherein the coloration of the glue is at a minimum level.

3. An adhesive for biological tissue according to claim 1, wherein the bifunctional or multifunctional aldehyde is selected from the group consisting of glyoxal, succinaldehyde, glutaraldehyde, and malealdehyde.

4. An adhesive for biological tissue according to claim 1, wherein the glue agent comprises a further component for enhancing the cross-linking rate and/or for adjusting the viscosity of the glue agent.

5. An adhesive for biological tissue according to claim 4, wherein the further component comprises a chitosan which is used for medical purposes.

6. An adhesive for biological tissue according to claim 2, wherein the bifunctional or multifunctional aldehyde is selected from the group consisting of glyoxal, succinaldehyde, glutaraldehyde, and malealdehyde.

7. An adhesive for biological tissue according to claim 2, wherein the glue agent comprises a further component for enhancing the cross-linking rate and/or for adjusting the viscosity of the glue agent.

8. An adhesive kit for biological tissue, comprising:

a first container containing recombinant human serum albumin, which is free of dimers, polymers, and any decomposed matters that have a molecular weight of about 43,000 and is free of infectious agents, as a main component; and a second container containing an aldehyde as a main component.

* * * * *